United States Patent
Taylor et al.

(10) Patent No.: US 10,517,678 B2
(45) Date of Patent: Dec. 31, 2019

(54) SYSTEM AND METHOD FOR DIAGNOSIS AND ASSESSMENT OF CARDIOVASCULAR DISEASE BY COMPARING ARTERIAL SUPPLY CAPACITY TO END-ORGAN DEMAND

(71) Applicant: HeartFlow, Inc., Redwood City, CA (US)

(72) Inventors: Charles A. Taylor, Menlo Park, CA (US); Hyun Jin Kim, San Mateo, CA (US); Sophie Khem, San Francisco, CA (US); Sethuraman Sankaran, Palo Alto, CA (US); David Spain, San Mateo, CA (US); Nan Xiao, Redwood City, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 15/192,286

(22) Filed: Jun. 24, 2016

(65) Prior Publication Data
US 2017/0095292 A1 Apr. 6, 2017

Related U.S. Application Data

(60) Provisional application No. 62/236,707, filed on Oct. 2, 2015.

(51) Int. Cl.
*A61B 34/10* (2016.01)
*G16H 50/50* (2018.01)
(Continued)

(52) U.S. Cl.
CPC ............ *A61B 34/10* (2016.02); *A61B 5/0044* (2013.01); *A61B 5/02028* (2013.01);
(Continued)

(58) Field of Classification Search
None
See application file for complete search history.

(56) References Cited

U.S. PATENT DOCUMENTS

| 6,908,435 B1 | 6/2005 | Mueller |
| 8,157,742 B2 | 4/2012 | Taylor et al. |

(Continued)

FOREIGN PATENT DOCUMENTS

| EP | 2690598 | 1/2014 |
| JP | 2013534154 A | 9/2013 |

(Continued)

OTHER PUBLICATIONS

Burton, Rebecca AB, et al. "Three- Dimensional Models of Individual Cardiac Histoanatomy: Tools and Challenges." Annals of the New York Academy of Sciences 1080.1 (2006): 301-319.*

(Continued)

*Primary Examiner* — Bijan Mapar
(74) *Attorney, Agent, or Firm* — Bookoff McAndrews, PLLC (57) ABSTRACT

Systems and methods are disclosed for to determining a blood supply and blood demand. One method includes receiving a patient-specific model of vessel geometry of at least a portion of a coronary artery, wherein the model is based on patient-specific image data of at least a portion of a patient's heart having myocardium; determining a coronary blood supply based on the patient-specific model; determining at least a portion of the myocardium corresponding to the coronary artery; determining a myocardial blood demand based on either a mass or a volume of the portion of the myocardium, or based on perfusion imaging of the portion of the myocardium; and determining a relationship between the coronary blood supply and the myocardial blood demand.

16 Claims, 7 Drawing Sheets

(51) Int. Cl.
| | |
|---|---|
| A61B 5/02 | (2006.01) |
| A61B 5/026 | (2006.01) |
| G16H 50/20 | (2018.01) |
| A61B 6/00 | (2006.01) |
| A61B 5/00 | (2006.01) |
| A61B 6/03 | (2006.01) |
| A61B 8/12 | (2006.01) |
| A61B 8/06 | (2006.01) |
| A61B 8/08 | (2006.01) |
| G16H 50/70 | (2018.01) |

(52) U.S. Cl.
 CPC .......... *A61B 5/0263* (2013.01); *A61B 6/032* (2013.01); *A61B 6/037* (2013.01); *A61B 6/503* (2013.01); *A61B 6/504* (2013.01); *A61B 6/507* (2013.01); *A61B 6/5217* (2013.01); *A61B 8/065* (2013.01); *A61B 8/12* (2013.01); *A61B 8/5223* (2013.01); *G16H 50/20* (2018.01); *G16H 50/50* (2018.01); *G16H 50/70* (2018.01); *A61B 5/0035* (2013.01); *A61B 5/0042* (2013.01); *A61B 5/02007* (2013.01); *A61B 5/7275* (2013.01); *A61B 8/0883* (2013.01); *A61B 8/0891* (2013.01); *A61B 2034/105* (2016.02); *A61B 2576/023* (2013.01)

(56) References Cited

U.S. PATENT DOCUMENTS

| | | | |
|---|---|---|---|
| 8,311,748 | B2 | 11/2012 | Taylor et al. |
| 8,315,814 | B2 | 11/2012 | Taylor et al. |
| 8,386,188 | B2 | 2/2013 | Taylor et al. |
| 8,594,950 | B2 | 11/2013 | Taylor et al. |
| 8,734,357 | B2 | 5/2014 | Taylor et al. |
| 8,903,472 | B2 | 12/2014 | Kassab |
| 9,087,147 | B1 | 7/2015 | Fonte |
| 2012/0072190 | A1* | 3/2012 | Sharma et al. .......... G06G 7/60 703/2 |
| 2013/0054214 | A1* | 2/2013 | Taylor ................ A61B 5/02007 703/9 |
| 2014/0029835 | A1* | 1/2014 | Kim .................... A61B 5/0044 382/134 |
| 2015/0250395 | A1* | 9/2015 | Igarashi ................... A61B 5/02 600/485 |
| 2015/0297161 | A1* | 10/2015 | Grass et al. ............. A61B 6/00 600/426 |
| 2017/0105694 | A1* | 4/2017 | Grass et al. ............. A61B 6/00 600/431 |
| 2017/0286628 | A1* | 10/2017 | Shim ...................... G06F 19/00 703/2 |

FOREIGN PATENT DOCUMENTS

| | | |
|---|---|---|
| JP | 2013233369 A | 11/2013 |
| JP | 2014128650 A | 7/2014 |

OTHER PUBLICATIONS

Kim, Kyung Hwan, et al. "Patient-specific coronary artery blood flow simulation using myocardial volume partitioning." SPIE Medical Imaging. International Society for Optics and Photonics, 2013.*

Ehara, S., Matsumoto, K., Shirai, N., Nakanishi, K., Otsuka, K., Iguchi, T., . . . & Yoshiyanna, M. (2013). Typical coronary appearance of dilated cardiomyopathy versus left ventricular concentric hypertrophy: coronary volumes measured by multislice computed tomography. Heart and vessels, 28(2), 188-198. (Year: 2013).*

(Sugimachi, M., & Kawada, T. (2009). Coronary Artery Volume Noninvasively Measured With Multislice Computed Tomography. Circulation Journal, 73(8), 1395-1396. (Year: 2009).*

Ehara, S., Okuyama, T., Shirai, N., Sugioka, K., Oe, H., Itoh, T., . . . & Hozumi, T. (2009). Inadequate Increase in the Volume of Major Epicardial Coronary Arteries Compared With That in Left Ventricular Mass. Circulation Journal, 73(8), 1448-1453. (Year: 2009).*

Zhou et al., "In vivo validation of the design rules of the coronary arteries and their application in the assessment of diffuse disease" Physics in Medicine and Biology, v01. 47, pp. 977-993, 2002.

Huo Y, Wischgoll T, Choy JS et al. CT-based diagnosis of diffuse coronary artery disease on the basis of scaling power laws. Radiology 2013;268:694-701.

Gould KL. Does coronary flow trump coronary anatomy? JACC Cardiovascular imaging 2009;2:1009-23.

Choy, J.S. and G.S. Kassab, Scaling of myocardial mass to flow and morphometry of coronary arteries. J Appl Physiol, 2008. 104(5): p. 1281-6.

International Search Report and the Written Opinion of the International Searching Authority received in related PCT/US2016/044895, dated Oct. 26, 2016; 12 pages.

* cited by examiner

SYSTEM AND METHOD FOR DIAGNOSIS AND ASSESSMENT OF CARDIOVASCULAR DISEASE BY COMPARING ARTERIAL SUPPLY CAPACITY TO END-ORGAN DEMAND

RELATED APPLICATION(S)

This application claims priority to U.S. Provisional Application No. 62/236,707 filed Oct. 2, 2015, the entire disclosure of which is hereby incorporated herein by reference in its entirety.

FIELD OF THE DISCLOSURE

Various embodiments of the present disclosure relate generally to disease assessment, treatment planning, and related methods. More specifically, particular embodiments of the present disclosure relate to systems and methods for assessing cardiovascular disease by comparing arterial supply capacity to end-organ demand.

BACKGROUND

Coronary artery disease is a common ailment that affects millions of people. Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina, during physical exertion or unstable angina when the patient is at rest. A more severe manifestation of disease may lead to myocardial infarction, or heart attack. Significant strides have been made in the treatment of coronary artery disease including both medical therapy (e.g. statins) or surgical alternatives (e.g., percutaneous coronary intervention (PCI) and coronary artery bypass graft surgery (CABG)). Invasive assessments are commonly used to assess the type of treatment a patient may receive. However, indirect or noninvasive assessments for formulating a patient treatment are being explored and developed.

Heart disease is typically viewed as resulting from vessel disease, in particular, narrowing or blockage inside vessel lumens in a way that impacts blood flow. Currently, treatment assessment takes into account such intraluminal factors. However, a desire exists to improve the diagnosis and/or treatment of cardiovascular disease by better assessing the severity of disease.

The foregoing general description and the following detailed description are exemplary and explanatory only and are not restrictive of the disclosure.

SUMMARY

According to certain aspects of the present disclosure, systems and methods are disclosed for using a relationship between arterial blood supply and organ or tissue demand to guide diagnosis or treatment of cardiovascular disease.

Systems and methods are disclosed for to determining a blood supply and blood demand. One method and/or system includes steps of receiving a patient-specific model of vessel geometry of at least a portion of a coronary artery, wherein the model may be based on patient-specific image data of at least a portion of a patient's heart having myocardium; determining a coronary blood supply based on the patient-specific model; determining at least a portion of the myocardium receiving blood from the coronary artery; determining a myocardial blood demand based on either a mass or a volume of the portion of the myocardium, or based on perfusion imaging of the portion of the myocardium; and determining a relationship between the coronary blood supply and the myocardial blood demand.

Other methods and systems may further comprise evaluating the patient based upon the determined relationship between the coronary blood supply and the myocardial blood demand.

Other methods and systems may further comprise determining whether a mismatch exists between the coronary blood supply and the myocardial blood demand based on the determined relationship between the coronary blood supply and the myocardial blood demand.

Other methods and systems may further comprise, based on the determination of whether the mismatch exists, modifying at least one parameter of a patient-specific simulation of blood flow through at least the portion of the coronary artery.

Other methods and systems may further comprise comparing the relationship to a reference value.

Other methods and systems may determine the reference value from a population of patients.

Other methods and systems may further comprise receiving a second patient-specific model representing coronary arterial vasculature downstream from the portion of the coronary artery.

In methods and systems herein, the mass of the portion of the myocardium may be calculated by measuring or assuming a tissue density of the portion of the myocardium, and multiplying the tissue density by the volume of the portion of the myocardium.

In methods and systems herein, the patient-specific model may be generated by modifying a generic model of vessel geometry.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Coronary artery disease is a common ailment, by which blood flow to the heart may be restricted. While significant strides have been made in the treatment of coronary artery disease, the treatment is often misplaced or excessive. For example, patients often undergo invasive surgical treatments when medication may suffice. Patients are sometimes subjected to treatments that may not change their condition. In some situations, patients even undergo treatments that ultimately worsen their condition. Thus, a need exists to accurately assess the severity of cardiovascular disease in selecting a course of treatment.

When assessing cardiovascular disease, and diseases of other organs and tissues in a patient, it is believed that for healthy individuals, the caliber of the arterial tree is sized appropriately to meet the demands of the tissue and organ supplied. For example, in the coronary arterial tree, large arteries on the epicardial surface of the heart, the epicardial coronary arteries, are assumed to conduct flow to the heart muscle (myocardium) through the smaller arteries, arterioles and capillaries with only minimal resistance to flow and, as a result, small gradients in pressure. Moreover, it is generally assumed that myocardial ischemia, a lack of blood flow to the muscle of the heart, is caused by either focal or diffuse atherosclerosis in the epicardial coronary arteries or microvascular dysfunction, i.e., an inability of the microcirculation to dilate in response to an increased demand for flow. These assumptions on the idealized relationship between myocardial tissue demand and the supply capacity of the epicardial coronary arteries, has led to a focus on diagnosing coronary artery disease on either the presence of obstructive anatomic disease in the coronary arteries using invasive coronary angiography (ICA), Intravascular Ultrasound (IVUS), invasive Fractional Flow Reserve (FFR), coronary computed tomography angiography (CCTA), noninvasive Fractional Flow Reserve derived from CT ($FFR_{CT}$), or on functionally significant disease assessed using myocardial perfusion imaging (MPI) using Single Photon Computed Emission Tomography (SPECT), Positron Emission Tomography (PET), Magnetic Resonance Perfusion Imaging (MRMPI), or Computed Tomography Perfusion imaging (CTP).

There has been a lack of understanding of and diagnostic methods to examine the relationship between the supply capacity of the coronary arteries and the end-organ demand of the myocardial muscle. There are many patients that present to the emergency department or their primary care doctors or cardiologists complaining of symptoms suggestive of coronary artery disease that, upon testing, have normal ICA and CCTA anatomic tests, but abnormal functional tests. Furthermore, there is a gap in functional testing, whereby methods to examine epicardial disease, such as FFR and $FFR_{CT}$, are generally ordered only when there is evidence of obstructive coronary artery disease narrowing the blood vessel. As a result, some patients that have symptoms of heart disease receive an improper or inadequate diagnosis as a result of the lack of a method to examine the relationship between coronary supply and myocardial demand. Novel techniques presented herein may be used to more accurately diagnose artery disease by analyzing the relationship between coronary supply and myocardial demand.

Figure 1:
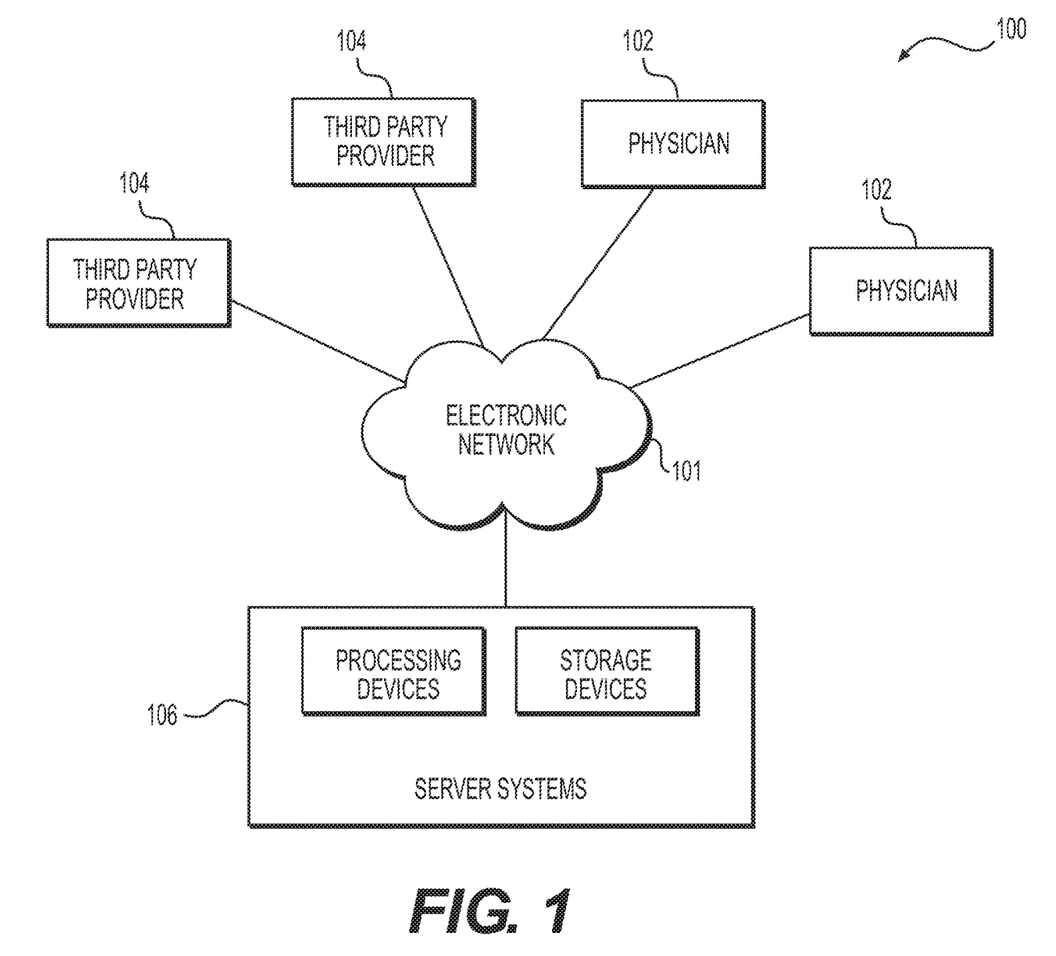
FIG. 1 is a block diagram of an exemplary system and network for assessing a patient based on analysis of blood supply and organ or tissue demand, according to an exemplary embodiment of the present disclosure.

Referring now to the figures, FIG. 1 depicts a block diagram of an exemplary system 100 and network for assessing a patient based on analysis of blood supply and organ or tissue demand, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices.

Figure 2A:
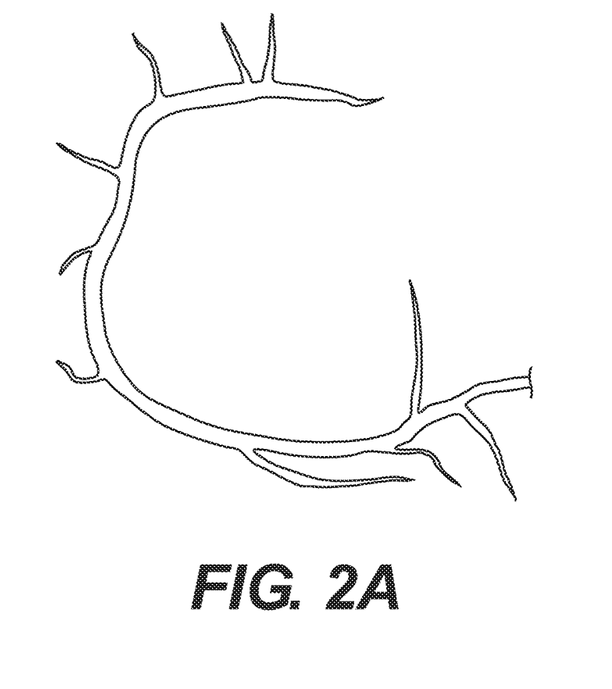
FIGS. 2A and 2B are images of arteries of patients obtained using an imaging device.
Figure 2B:
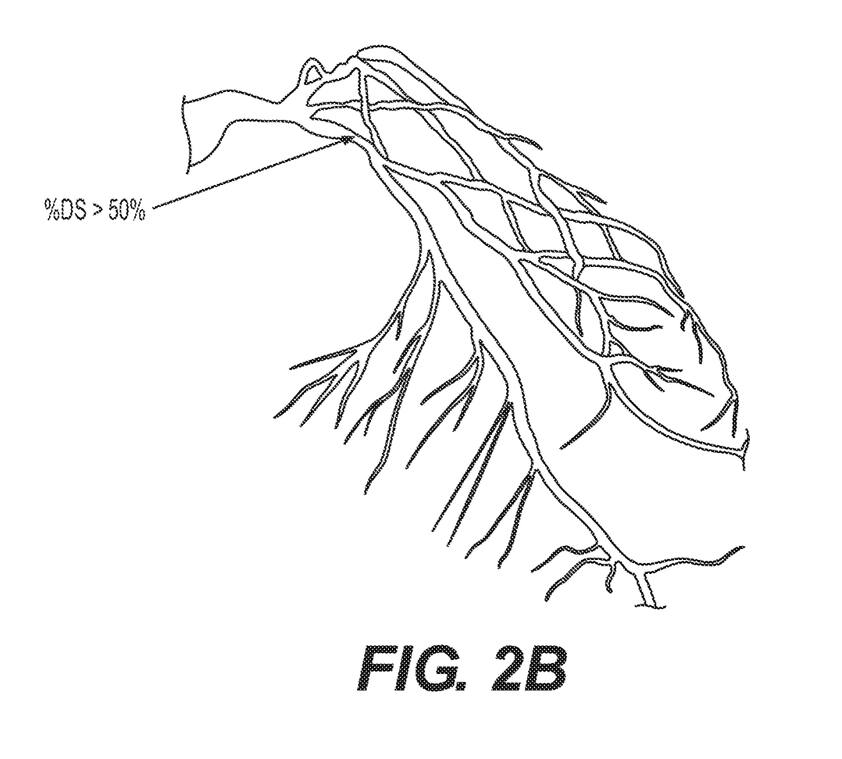

FIGS. 2A and 2B are images of coronary arteries obtained from patients using an imaging device. The image data of FIGS. 2A and 2B may be captured, processed, and/or stored by server systems 106. The image data may be based on information, images, and/or data received from physicians 102 and/or third party providers 104 over electronic network 101.

As shown in FIGS. 2A and 2B, anatomic data may be obtained noninvasively using, for example, coronary computed tomographic angiography (CCTA). CCTA may be used for imaging of patients with chest pain and involves using computed tomography (CT) technology to image the heart and the coronary arteries following an intravenous infusion of a contrast agent. However, CCTA also cannot provide direct information on the functional significance of coronary lesions, e.g., whether the lesions affect blood flow. In addition, since CCTA is purely a diagnostic test, it cannot be used to predict changes in coronary blood flow, pressure, or myocardial perfusion under other physiologic states, e.g., exercise, nor can it be used to predict outcomes of interventions.

Thus, patients may also require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Rather, a doctor may insert a stent because, as shown in FIG. 2B, a portion of an artery appears that it has a substantial degree of stenosis (DS), for example, the degree of stenosis is greater than 50% of the vessel lumen. Thus, CCA has led to what has been referred to as an "oculostenotic reflex" of some interventional cardiologists to insert a stent for every lesion found with CCA regardless of whether the lesion is functionally significant. As a result, CCA may lead to unnecessary operations on the patient, which may pose added risks to patients and may result in unnecessary heath care costs for patients. Techniques presented herein may remedy one or more of these problems by determining a relationship between blood supply and organ or tissue demand.

Figure 3:
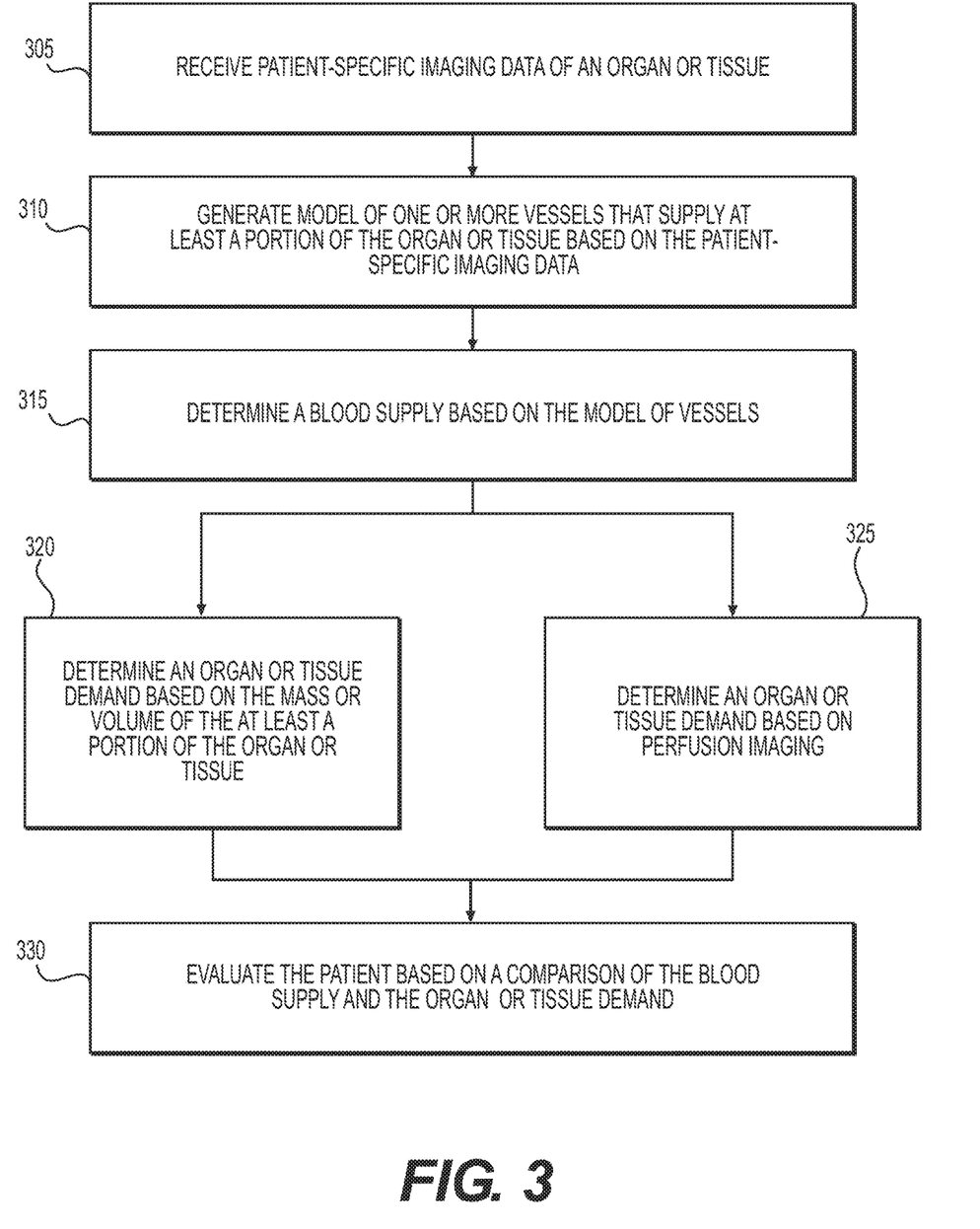
FIG. 3 is a block diagram of an exemplary method of determining a relationship between coronary blood supply and organ or tissue blood demand, according to an exemplary embodiment of the present disclosure.
Figure 4:
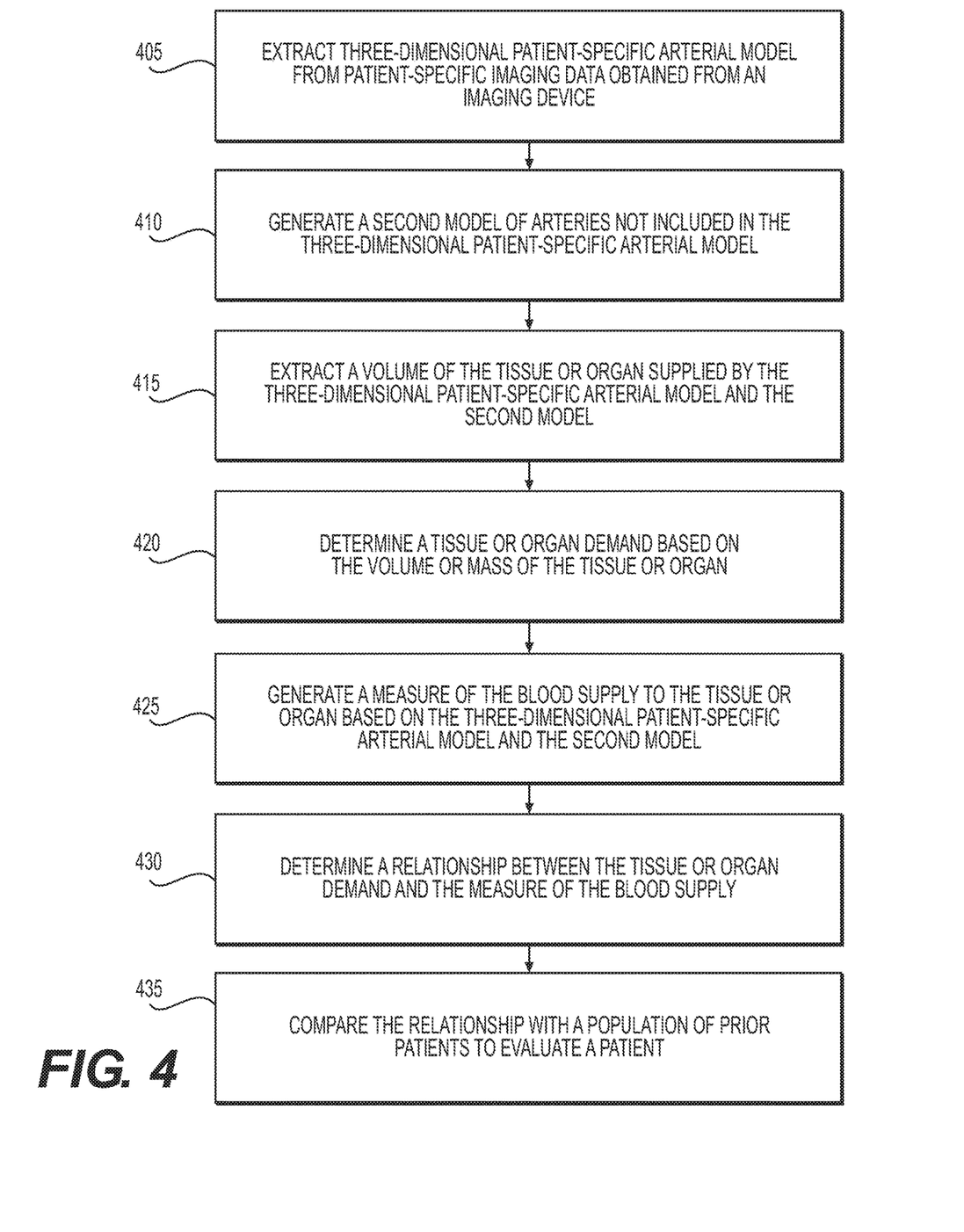
FIG. 4 is a block diagram of an exemplary method of comparing a patient-specific relationship between arterial blood supply and organ or tissue blood demand to that of a population of prior patients, according to an exemplary embodiment of the present disclosure.
Figure 5:
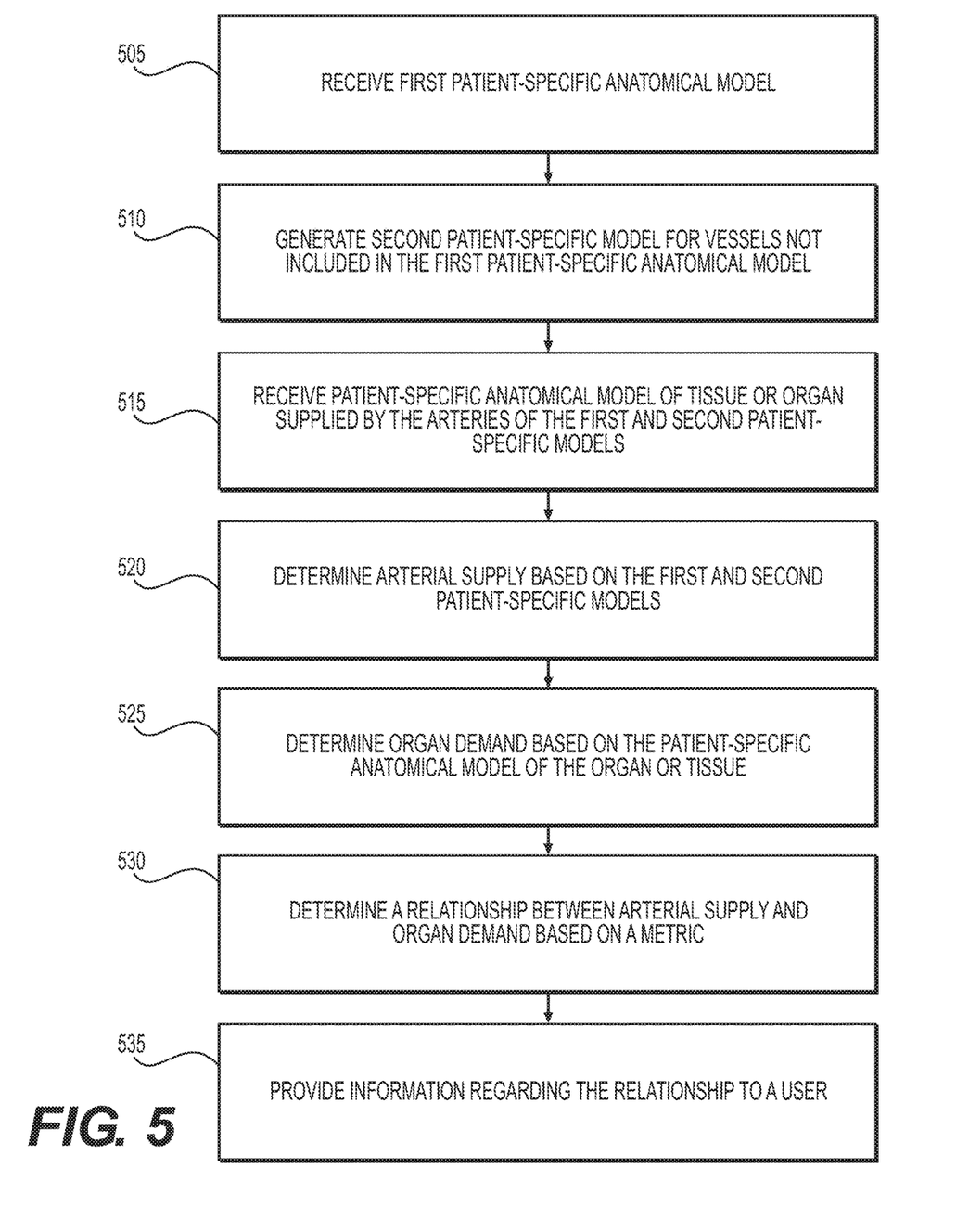
FIG. 5 is a block diagram of an exemplary method of determining a relationship between arterial blood supply and organ or tissue blood demand, according to an exemplary embodiment of the present disclosure.
Figure 6:
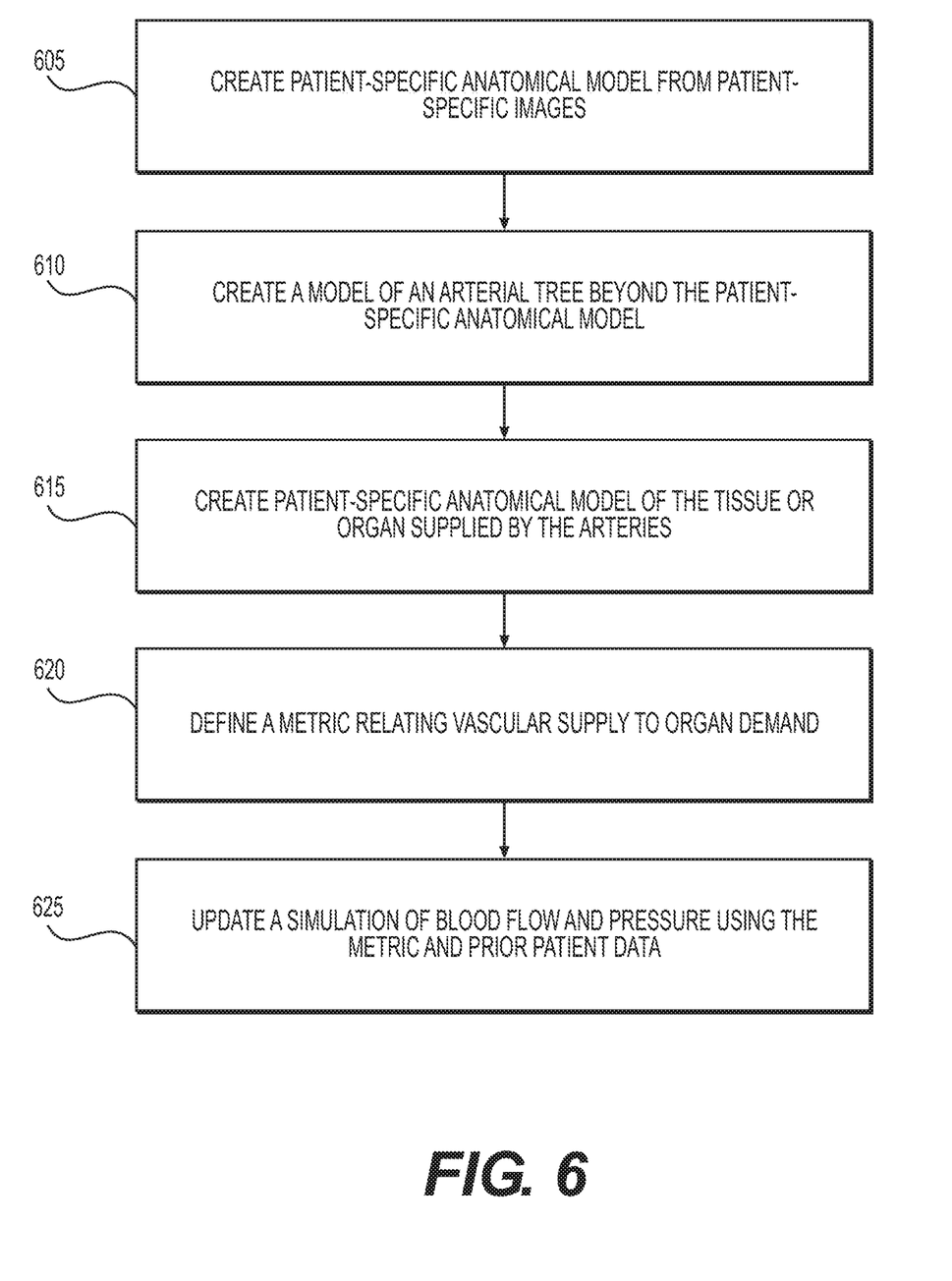
FIG. 6 is a block diagram of an exemplary method of determining a relationship between arterial blood supply and organ or tissue blood demand to update a simulation of blood flow and pressure, according to an exemplary embodiment of the present disclosure.
Figure 7:
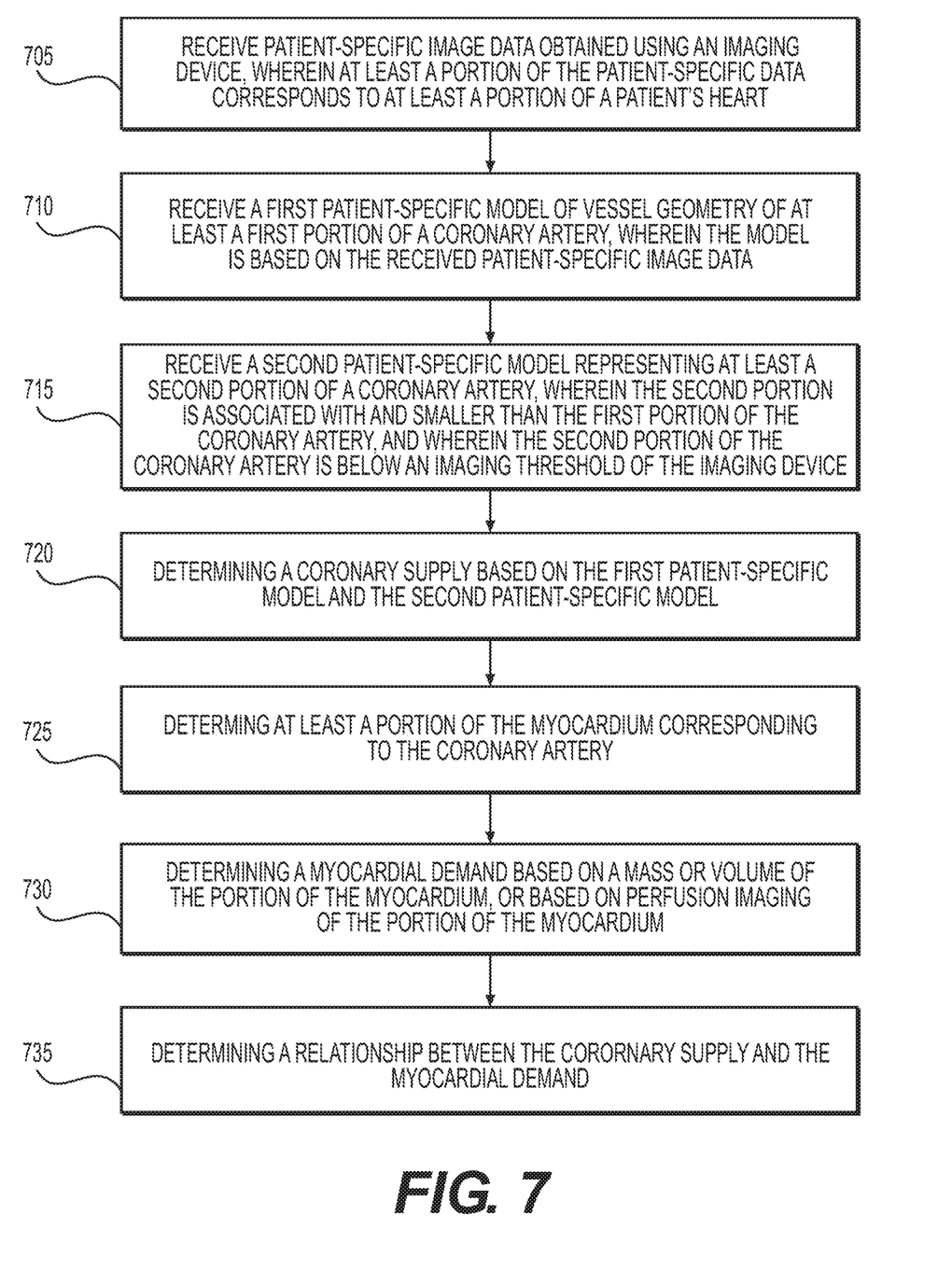
FIG. 7 is a block diagram of an exemplary method of determining a coronary supply and myocardial demand, according to an exemplary embodiment of the present disclosure.

FIG. 3 is a block diagram of an exemplary method of determining a relationship between coronary blood supply and organ or tissue blood demand. FIG. 4 is a block diagram of an exemplary method of comparing a patient-specific relationship between arterial blood supply and organ or tissue blood demand to that of a population of prior patients. FIG. 5 is a block diagram of an exemplary method of determining a relationship between arterial blood supply and organ or tissue blood demand. FIG. 6 is a block diagram of an exemplary method of determining a relationship between arterial blood supply and organ or tissue blood demand to update a simulation of blood flow and pressure. FIG. 7 is a block diagram of an exemplary method of determining a coronary supply and myocardial demand.

In contrast with conventional techniques, embodiments of the present disclosure may determine a relationship between arterial blood supply and organ or tissue blood demand in order to more accurately assess vascular health. FIG. 3 is a block diagram of an exemplary method of determining a relationship between coronary blood supply and myocardial blood demand, according to an exemplary embodiment of the present disclosure. The method of FIG. 3 may be performed by server systems 106, based on information, images, and data received from physicians 102 and/or third party providers 104 over electronic network 101.

In one embodiment, step 305 may include receiving patient-specific imaging data of an organ or tissue. In an embodiment, using coronary CT angiography or other imaging technique, the coronary arteries and the muscle of the heart, the myocardium, may both be imaged.

At step 310, a model of one or more vessels that supply blood to at least a portion of the organ or tissue may be generated based on the patient-specific imaging data. Techniques disclosed herein may extract the geometry of the epicardial coronary arteries from the coronary CT angiography data, and append a theoretical model representing the small arteries and arterioles that cannot be imaged in vivo. The theoretical model may be based on prior patient data, and/or may be selected based on the patient-specific imaging data.

At step 315, a blood supply may be determined based on the model of one or more vessels. For example, the total volume of the coronary arterial tree may be computed. The above-mentioned theoretical model may represent the arteries and arterioles which are smaller than a known imaging threshold for the imaging device used to obtain patient-specific imaging data, and may be included in the determination of blood supply. Blood flow through the coronary arteries may be determined, and may be assumed to be related to the total coronary volume to the ¾ power, although another mathematical relationship may be used.

At steps 320 and 325, an organ or tissue demand may be determined. At step 320, for example, demand may be determined based on a mass or volume of the at least a portion of the organ or tissue. This may be the portion of the organ or tissue which is supplied with blood by the vessels corresponding to the model determined above. For example, the determined flow through the coronary arteries may be assumed to be related to the myocardial mass or volume to the ¾ power, although the exact power or mathematical relationship used may vary. Thus, for example, the ratio of coronary volume to myocardial mass may be used to determine a mismatch between coronary supply and myocardial demand indicative of disease or a small caliber coronary arterial tree relative to the tissue mass that needs to be perfused.

Using either or both steps 320 and 325, the demand for blood of at least a portion of an organ or tissue may be determined. As discussed above, at step 320, demand for an organ or tissue may be determined based on a mass or volume of at least a portion of an organ or tissue. At step 325, the organ or tissue demand, such as the demand of at least a portion of the myocardium, may be determined based on perfusion imaging. At step 330, and as will be further disclosed in other embodiments presented herein, the patient may be evaluated based on a comparison of the blood supply determined at step 315, and the organ or tissue demand determined at steps 320 and/or 325. For example, the ratio of blood supply to corresponding organ or tissue blood demand may indicate a presence or lack of ischemia.

This approach is not necessarily limited to the coronary arteries, or to CT imaging. This may be applied to other organs and tissues, e.g. blood flow to the brain, kidneys, liver, legs, arms, etc. Imaging techniques may vary. For example, the anatomic data to extract an arterial model may be obtained using 2D conventional angiography, 3D rotational angiography, magnetic resonance imaging, or 2D or 3D ultrasound imaging. Organ volume may be obtained using magnetic resonance imaging, or 2D or 3D ultrasound imaging, for example. Organ or tissue demand may be defined from organ or tissue volume, or organ or tissue mass (which may be computed using the volume data and a measured or assumed organ or tissue density). Organ or tissue demand may also be assessed directly using perfusion imaging from CT, MR, PET, or SPECT, or indirectly from CT, MRI or echocardiographic wall motion data using a model relating cardiac dynamics and work to blood flow demand.

FIG. 4 is a block diagram of an exemplary method of comparing a patient-specific relationship between arterial blood supply and organ or tissue blood demand to that of a population of prior patients, according to an exemplary embodiment of the present disclosure. The method of FIG. 4 may be performed by server systems 106, based on information, images, and data received from physicians 102 and/or third party providers 104 over electronic network 101.

In one embodiment, as shown in step 405, a three-dimensional patient-specific arterial or anatomic model may be extracted from patient-specific imaging data, such as imaging data from an imaging device. At step 410, a second model of arteries not included in the three-dimensional patient-specific arterial model may be generated. For example, a model of the arteries beyond the limits of the imaging resolution of the imaging device may be generated. The model may be determined using branching laws originating from the terminal vessels extracted from the image data, or by generating vessels to fit within the boundaries of the supplied tissue extracted from the imaging data. At step 415, a volume or mass of the relevant tissue of the organ supplied may also be extracted from imaging data. For example, a volume or mass of the tissue or organ supplied by the three-dimensional patient-specific arterial model and the second model may be extracted. The volume or mass may be extracted using image processing methods where the organ surfaces are extracted. At step 420, the volume or mass of the tissue or organ may be used to determine a tissue or organ demand. This may be done by relating the mass or volume of the tissue or organ to a physiologic parameter using form-function relations. In one embodiment, total coronary artery blood flow is related to myocardial mass to determine demand of the heart for blood. At step 425, a measure of the blood supply to the tissue or organ may be generated based on the three-dimensional patient-specific arterial model and the second model. This may be performed by segmenting the (inner) luminal surface of the blood vessel, computing the luminal volume and relating flow to the calculated volume. At step 430, a relationship between the tissue or organ demand and the measure of the blood supply may be determined. For example, the ratio of coronary arterial lumen volume to myocardial mass may be calculated. At step 435, the relationship may be compared with a population of prior patients for patient evaluation purposes. For example, a relationship between a measure of the supplying arteries to a measure of the organ demanding blood may be calculated, reported, and compared to a normal reference value derived from a population of prior patients using statistical methods or machine learning. This comparison of the derived metric from the individual to the expected value from a population may then be used clinically to diagnose disease in the individual patient. The ratio of coronary arterial lumen volume to myocardial mass may be predictive of limitations in coronary artery blood flow to the heart muscle, which may for example cause chest pain.

Techniques presented herein may use metrics related to a measure of the capacity of the supplying arteries to a measure of the organ demanding blood to refine the physiologic boundary conditions for an individual patient for use in patient-specific modeling of blood flow. For example, the ratio of vascular volume to organ mass could be calculated for an individual patient, compared to data from a population of patients, and used to increase or decrease the resistance to flow under baseline, hyperemic, or exercise conditions. This could be applied to the calculation of noninvasive fractional flow reserve or coronary flow reserve to improve the accuracy of these methods for an individual patient. For example, in one embodiment, machine learning methods could be used together with information on the coronary artery lumen volume to myocardial mass ratio and measured FFR values in different patients to identify how the resistance boundary conditions could be adjusted to improve the accuracy of predictions of computed FFR.

FIG. 5 is a block diagram of an exemplary method of determining a relationship between arterial blood supply and organ or tissue blood demand, according to an exemplary embodiment of the present disclosure. The method of FIG. 5 may be performed by server systems 106, based on information, images, and data received from physicians 102 and/or third party providers 104 over electronic network 101.

At step 505, a first patient-specific anatomic model may be received. The model may correspond to arteries of a patient, and may be received from an imaging device, or an electronic storage device (e.g., a hard drive, network drive, etc.). At step 510, a second patient-specific model may be generated for vessels not included in the first patient-specific anatomic model. For example, the second patient-specific model may include small blood vessels not observable in the image due to the limits of image resolution, image quality or limitations of the data collection technique.

At step 515, one or more patient-specific anatomic models of tissue or an organ supplied by the arteries of the first and second patient-specific models may be received or generated. The one or more models may be received from an electronic storage device (e.g., a hard drive, network drive, etc.).

Similar to techniques presented above, at step 520, the arterial supply may be determined based on the first and second patient specific models. At step 525, organ or tissue demand may be determined based on the patient-specific anatomic model of the organ or tissue. Optionally, the organ or tissue mass may be calculated by measuring or assuming a tissue density and multiplying it by the tissue/organ volume. Alternatively, tissue or organ demand may be computed using methods described above.

At step 530, a relationship between arterial supply and organ demand may be determined based on a metric. In an embodiment, this metric could be the ratio of the volume of the first patient-specific model to the volume or mass of the tissue/organ for the patient, or the ratio of the sum of the first and second patient-specific volumes to the volume or mass of the tissue/organ for that same patient.

At step 535, information may be provided on one or more parameters describing the relationship between arterial supply and tissue/organ demand. This information may be displayed to a user through a report, visual display or written to an electronic storage device (e.g., hard disk, network drive, cloud storage, smart phone, tablet, etc.).

In some embodiments of techniques described herein, the supply-to-demand metric(s) computed for an individual patient above may be compared to data from a population of patients to provide additional information as to whether the patient data is within the normal range for an appropriate demographic. In general, the normal supply-to-demand metric(s) may also depend on patient characteristics such as age, gender, blood pressure etc. This relationship can be inferred from data that relates all of these characteristics, including the supply-to-demand metrics, to whether the patient is healthy or diseased.

In some embodiments of techniques described herein, the supply-to-demand metric(s) computed for an individual patient above may be utilized to update the physiologic model for that individual patient and/or compute blood flow and pressure, total or regional tissue perfusion, Fractional Flow Reserve (FFR), Coronary Flow Reserve (CFR), Index of Microcirculatory Resistance (IMR), territory at risk, plaque rupture risk, and/or plaque stress. Machine learning methods may be used to learn how the supply-to-demand metric(s) could be factored into boundary conditions assigned to compute coronary flow and pressure. For example, values of the supply-to-demand metrics that indicate that blood flow is too large to compute FFR accurately, may be used to change the boundary conditions in the calculation to decrease the flow. This data could be used in conjunction with machine-learning methods to augment the predictive capability of those methods. For example, a particular supply-to-demand ratio may be indicative of a certain resistance to flow, as will be discussed further below. The resistance may be used to configure a patient-specific model which may be used to simulate blood flow in a patient's organs and/or tissues.

FIG. 6 is a block diagram of an exemplary method of determining a relationship between arterial blood supply and organ or tissue blood demand to update a simulation of blood flow and pressure, according to an exemplary embodiment of the present disclosure. The method of FIG. 6 may be performed by server systems 106, based on information, images, and data received from physicians 102 and/or third party providers 104 over electronic network 101.

At step 605, one or more patient-specific anatomical models may be created from patient-specific images. Techniques presented herein may construct the patient-specific anatomic model from two-dimensional (e.g. coronary angiography, biplane angiography) or three-dimensional (e.g. 3D rotational angiography, coronary computed tomographic angiography (CCTA), magnetic resonance angiography (MRA)) model. This step may include methods to directly segment the image data and create a patient-specific three-dimensional anatomic model of the patient's arteries, or may involve modifying a previously-constructed "generic" model to customize it for that patient and create a patient-specific model. In either case, the patient-specific anatomic model may include some or all information related to the arteries of interest, including the length of each segment, diameter along the length of a segment (or any other geometrical description of the segment), branching patterns, presence of disease and/or characteristics of disease including composition of atherosclerotic plaques. The representation of the model may be defined by a surface enclosing a three-dimensional volume, a one-dimensional model where the centerline of the vessels is defined together with cross-sectional area information along the length, or could be an implicit representation of the vessel surface. The anatomic model may represent many different kinds of anatomy, such as coronary arteries, peripheral arteries, cerebral arteries, visceral arteries, hepatic vessels, renal arteries, etc. The model may also be received prior to using the methods and systems described herein.

At step 610, a model of the arterial tree beyond the anatomic model discussed above may be created. In an embodiment, an anatomic model of the coronary arteries may be created downstream of the outlets of the model created above based on the theoretical anatomy of the coronary arteries by, for example, using data from the literature on coronary artery branching patterns. Alternatively, this model could also use the measured organ volume and boundaries to constrain the generated network of vessels as described in U.S. Pat. Nos. 8,386,188 and 8,315,814, both of which are incorporated herein by reference.

At step 615, a patient-specific anatomic model of the tissue or organ supplied by the arteries of the first and second patient-specific models may be generated. In one embodiment, this is a model of the entire heart, the individual chamber tissue volumes, or the left ventricle myocardium extracted from CCTA imaging data. This model may be used to estimate organ demand for blood.

At step 620, a metric relating vascular supply to organ demand may be defined or determined. In one embodiment, this metric is the ratio of the epicardial coronary artery volume (calculated in the step above) or the total coronary arterial volume (calculated in steps above) to myocardial mass, i.e., volume/mass. A low volume to mass ratio may be associated with presence of ischemia, whereas a higher volume to mass ratio may be associated with absence of ischemia. For example, a ratio of volume/mass, using units $mm^3/g$, of 30 or above may be associated with absence of ischemia. A ratio of below 30, and especially below 15, may be associated with presence of ischemia. As another example, a ratio above 30 may be classified as non-ischemic, 30-15 as moderately ischemic, and below 15 as ischemic. The specific thresholds, number and type of categorizations may vary. This metric may be determined in a similar manner using any vessels, organs or tissue.

The supply-to-demand metrics may also be useful in predicting coronary flow reserve (CFR). For example, it is expected that low values of CFR would be observed in patients with low values of supply-to-demand metrics. A ratio of volume/mass, using units $mm^3/g$, of below 30, and especially below 15, may be associated with low coronary flow reserve.

Another step of techniques presented herein may be to report the above-calculated metric to a patient, physician or health care provider.

At step 625, a simulation of blood flow and pressure may be updated using the above calculated metric in comparison to population-based data to refine the physiologic model. This may be performed by adjusting values for microvascular resistance based on the above calculated metric.

While one embodiment is related to more accurately computing blood flow and pressure in the human coronary arteries, other embodiments may include computing blood flow and pressure in the extracranial and intracranial cerebral arteries, the lower extremity arteries including the iliac, superficial femoral, common femoral, tibial, popliteal, peroneal, pedal arteries in patients with peripheral arterial disease, the renal arteries, the mesenteric arteries, and/or other vascular beds. This may be used to improve the methods described in U.S. Pat. Nos. 8,386,188 and 8,315,814, incorporated by reference in their entirety, which relate to simulating perfusion in the heart and brain, respectively.

In addition, techniques presented herein may cause an improved calculation of blood flow and pressure which could improve the prediction of plaque rupture as, for example, described in U.S. Pat. No. 8,311,748, which is incorporated by reference in its entirety. These techniques may result in more accurate predictions of baseline conditions that could then be used in treatment planning for example as described in U.S. Pat. Nos. 8,157,742, 8,594,950, and 8,734,357, which are incorporated by reference in their entirety. This method can also be repeated with/without vasodilating drugs to assess the dilatory capacity of the epicardial arteries/microvasculature.

FIG. 7 is a block diagram of an exemplary method of determining a coronary supply and myocardial demand, according to an exemplary embodiment. The method of FIG. 7 includes steps of many of the prior-described embodiments, and applies those steps specifically to the heart and coronary arteries. Any of the details of corresponding steps in earlier-described embodiments may be used in the FIG. 7 method. The method of FIG. 7 may be performed by server systems 106, based on information, images, and data received from physicians 102 and/or third party providers 104 over electronic network 101.

At step 705, patient-specific image data obtained using an imaging device may be received, wherein at least a portion of the patient-specific image data corresponds to at least a portion of a patient's heart. At step 710, a first patient-specific model of vessel geometry of at least a first portion of a coronary artery may be received, wherein the model is based on the received patient-specific image data. At step 715, a second patient-specific model representing at least a second portion of a coronary artery may be received, wherein the second portion is associated with and smaller than the first portion of the coronary artery, and wherein the second portion of the coronary artery is below an imaging threshold of the imaging device. At step 720, a coronary supply based on the first patient-specific model and the second patient-specific model may be determined. At step 725, at least a portion of the myocardium corresponding to the coronary artery may be determined. At step 730, a myocardial demand based on a mass or volume of the portion of the myocardium, or based on perfusion imaging of the portion of the myocardium, may be determined. At step 735, a relationship between the coronary supply and myocardial demand may be determined.

For exemplary purposes, multiple embodiments are described herein. Any of the details of any steps of any embodiment described herein may be used with similar steps of other embodiments.

Techniques presented herein describe methods which may determine a relationship between blood supply to an organ or tissue, and blood demand from that organ or tissue. These techniques provide significant insight into the overall disease burden of patients with atherosclerosis which would have prognostic value.

Novel approaches described herein include determining a relationship between blood supply and blood demand in relationship to a given organ or tissue. Such a determination may be made for patients under resting, hyperemic and/or exercise conditions. These techniques may apply to the coronary arteries, but also to simulations of blood flow and pressure in any arterial tree including, but not limited to, the carotid, cerebral, renal, and lower extremity arteries.

Techniques presented herein may calculate the ratio of blood flow and resistance based on vascular volume to that based on myocardial volume or mass, and may be implemented and included in an FFRCT platform. Methods to compute and display the resting flow mismatch or update the set of physiologic conditions and boundary conditions of the patient using this data may also be performed.

Other embodiments of the invention will be apparent to those skilled in the art from consideration of the specification and practice of the invention disclosed herein. Numerous embodiments are discussed herein, which may be used in various combinations with each other. It is intended that the specification and examples be considered as exemplary only, with a true scope and spirit of the invention being indicated by the following claims.

What is claimed is:

1. A computer-implemented method of analyzing a relationship between a blood supply and a blood demand of a patient, the method comprising:
   receiving a patient-specific vascular model of vessel geometry of at least a portion of a coronary artery of the patient's heart, wherein the patient-specific vascular model is generated from patient-specific image data of at least a portion of the patient's heart;
   modeling a volume-based supply capacity of the patient's coronary artery based on the patient-specific vascular model, the volume-based supply capacity being the volume of the patient's coronary artery;
   determining a mass or a volume of at least a portion of a myocardium receiving blood from the patient's coronary artery;
   determining an amount of blood demanded by the determined mass or volume of the portion of the myocardium;
   comparing the modeled volume-based supply capacity of the patient's coronary artery to the determined amount of blood demanded by the determined mass or volume;
   generating a patient-specific simulation of blood flow through the patient-specific vascular model of at least the portion of the patient's coronary artery;
   updating the patient-specific simulation of blood flow by modifying a parameter of the patient-specific simulation of blood flow based on the comparison; and
   evaluating the patient based on the updated patient-specific simulation of blood flow.

2. The method of claim 1, wherein evaluating the patient includes determining a disease state of the patient based upon the comparison between an amount of blood supplied and the amount of blood demanded.

3. The method of claim 1, wherein the comparison includes one or more of:
   determining a difference between the modeled volume-based supply capacity of the patient's coronary artery and the determined amount of blood demanded, and
   comparing the modeled volume-based supply capacity of the patient's coronary artery to a reference value, or comparing the determined amount of blood demanded to a reference value.

4. The method of claim 3, wherein the comparison includes comparing the modeled volume-based supply capacity of the patient's coronary artery to a reference value determined from a population of patients, or comparing the determined amount of blood demanded to a reference value determined from a population of patients.

5. The method of claim 1, further comprising:
   receiving a second patient-specific vascular model representing coronary arterial vasculature downstream from the portion of the patient's coronary artery; and
   determining an amount of blood supplied by the patient's coronary artery, based on the patient-specific vascular model and the second patient-specific vascular model.

6. The method of claim 5, wherein the second patient-specific vascular model is generated based upon boundaries of a tissue associated with at least a portion of the patient's coronary artery.

7. The method of claim 1, wherein the mass of the portion of the myocardium is calculated by measuring or computing a tissue density of the portion of the myocardium, and multiplying the tissue density by the volume of the portion of the myocardium.

8. The method of claim 1, wherein the patient-specific vascular model is generated by modifying a generic model of vessel geometry.

9. A system for image processing to analyzing a relationship between a blood supply and a blood demand, the system comprising:
   a data storage device storing instructions for determining the blood supply and the blood demand; and
   a processor configured to execute the instructions to perform a method including:
      receiving a patient-specific vascular model of vessel geometry of at least a portion of a coronary artery of the patient's heart, wherein the patient-specific vascular model is generated from patient-specific image data of at least a portion of the patient's heart;
      modeling a volume-based supply capacity of the patient's coronary artery based on the patient-specific vascular model, the volume-based supply capacity being the volume of the patient's coronary artery;

determining a mass or a volume of at least a portion of a myocardium receiving blood from the patient's coronary artery;

determining an amount of blood demanded by the determined mass or volume of the portion of the myocardium;

comparing the modeled volume-based supply capacity of the patient's coronary artery to the determined amount of blood demanded by the determined mass or volume;

generating a patient-specific simulation of blood flow through the patient-specific vascular model of at least the portion of the patient's coronary artery;

updating the patient-specific simulation of blood flow by modifying a parameter of the patient-specific simulation of blood flow based on the comparison; and evaluating the patient based on the patient-specific simulation of blood flow.

10. The system of claim 9, wherein evaluating the patient includes determining a disease state of the patient.

11. The system of claim 9, wherein the comparison includes one or more of:

determining a difference between the modeled volume-based supply capacity of the patient's coronary artery and the determined amount of blood demanded, and comparing the modeled volume-based supply capacity of the patient's coronary artery to a reference value, or comparing the determined amount of blood demanded to a reference value.

12. The system of claim 11, wherein the comparison includes comparing the modeled volume-based supply capacity of the patient's coronary artery to a reference value determined from a population of patients, or comparing the determined amount of blood demanded to a reference value determined from a population of patients.

13. The system of claim 9, wherein the system is further configured for:

receiving a second patient-specific vascular model representing coronary arterial vasculature downstream from the portion of the patient's coronary artery; and determining an amount of blood supplied by the patient's coronary artery, based on the patient-specific vascular model and the second patient-specific vascular model.

14. The system of claim 13, wherein the second patient-specific vascular model is generated based upon boundaries of a tissue associated with at least a portion of the patient's coronary artery.

15. The system of claim 9, wherein the mass of the portion of the myocardium is calculated by measuring or computing a tissue density of the portion of the myocardium, and multiplying the tissue density by the volume of the portion of the myocardium.

16. A non-transitory computer readable medium for use on a computer system containing computer-executable programming instructions for performing a method of analyzing a relationship between a blood supply and a blood demand, the method comprising:

receiving a patient-specific vascular model of vessel geometry of at least a portion of a coronary artery of the patient's heart, wherein the patient-specific vascular model is generated from patient-specific image data of at least a portion of the patient's heart;

modeling a volume-based supply capacity of the patient's coronary artery based on the patient-specific vascular model, the volume-based supply capacity being the volume of the patient's coronary artery;

determining a mass or a volume of at least a portion of a myocardium receiving blood from the patient's coronary artery;

determining an amount of blood demanded by the determined mass or volume of the portion of the myocardium;

comparing the modeled volume-based supply capacity of the patient's coronary artery to the determined amount of blood demanded by the determined mass or volume;

generating a patient-specific simulation of blood flow through the patient-specific vascular model of at least the portion of the patient's coronary artery;

updating the patient-specific simulation of blood flow by modifying a parameter of the patient-specific simulation of blood flow based on the comparison; and evaluating the patient based on the patient-specific simulation of blood flow.

* * * * *